(12) United States Patent
Bray et al.

(10) Patent No.: US 8,613,772 B2
(45) Date of Patent: Dec. 24, 2013

(54) LATERAL MOUNT IMPLANT DEVICE

(75) Inventors: Robert S. Bray, Studio City, CA (US); James M. Moran, North Royalton, OH (US); Mark T. Whiteaker, Rocky River, OH (US)

(73) Assignee: RSB Spine LLC, Cleveland, OH (US)

( * ) Notice: Subject to any disclaimer, the term of this patent is extended or adjusted under 35 U.S.C. 154(b) by 1693 days.

(21) Appl. No.: 11/686,054

(22) Filed: Mar. 14, 2007

(65) Prior Publication Data

US 2007/0233253 A1 Oct. 4, 2007

Related U.S. Application Data

(63) Continuation-in-part of application No. 11/620,255, filed on Jan. 5, 2007, now Pat. No. 8,100,976, and a continuation-in-part of application No. 11/248,651, filed on Oct. 12, 2005, now Pat. No. 7,985,255, said application No. 11/620,255 is a continuation-in-part of application No. 10/419,652, filed on Apr. 21, 2003, now Pat. No. 6,984,234, said application No. 11/248,651 is a continuation-in-part of application No. 10/419,652.

(60) Provisional application No. 60/782,795, filed on Mar. 16, 2006.

(51) Int. Cl.
*A61F 2/44* (2006.01)

(52) U.S. Cl.
USPC ........................................................ 623/17.16

(58) Field of Classification Search
USPC .................. 623/17.11, 17.15–17.16; 606/280
See application file for complete search history.

(56) References Cited

U.S. PATENT DOCUMENTS

| | | |
|---|---|---|
| 4,599,086 A | 7/1986 | Doty |
| 4,904,261 A | 2/1990 | Dove et al. |
| 4,955,908 A | 9/1990 | Frey et al. |

(Continued)

FOREIGN PATENT DOCUMENTS

| | | |
|---|---|---|
| EP | 0179695 | 4/1986 |
| EP | 1103236 | 5/2001 |

(Continued)

OTHER PUBLICATIONS

Will F. Beringer, D.O.; Jean-Pierre Mobasser, M.D., "Unilateral Pedicle Screw Instrumentation for Minimally Invasive Transforaminal Lumber Interbody Fusion", Neurosurg Focus, 2006, 12 pages, www.medscape.com, American Association of Neurological Surgeo8.

(Continued)

*Primary Examiner* — Michael T Schaper
(74) *Attorney, Agent, or Firm* — Cooper Legal Group, LLC

(57) ABSTRACT

An implant device for the spine suitable for the fixation and support of adjacent vertebrae includes a base member for implantation at a location between the two vertebrae and one or more protrusions extending from the base member. The protrusion(s) are configured for engagement with one of the vertebrae upon implantation and for progressive penetration into the vertebrae over a period of time subsequent to the implantation. The implant device includes a lateral mounting portion to accommodate fixation of the device to a lateral side of the vertebrae. The implant device is configured for insertion between the adjacent vertebrae through a posterior lateral or lateral opening that exposes a lateral side of the disc space.

47 Claims, 9 Drawing Sheets

(56) References Cited

U.S. PATENT DOCUMENTS

| | | | |
|---|---|---|---|
| 5,364,399 A | 11/1994 | Lowery et al. | |
| 5,425,773 A | 6/1995 | Boyd et al. | |
| 5,645,599 A | 7/1997 | Samani | |
| 5,713,898 A | 2/1998 | Stucker et al. | |
| 5,713,899 A | 2/1998 | Marnay et al. | |
| 5,800,433 A | 9/1998 | Benzel et al. | |
| 5,865,846 A | 2/1999 | Bryan et al. | |
| 5,888,223 A | 3/1999 | Bray, Jr. | |
| 5,888,224 A | 3/1999 | Beckers et al. | |
| 6,019,793 A | 2/2000 | Perren et al. | |
| 6,066,175 A | 5/2000 | Henderson et al. | |
| 6,193,721 B1 | 2/2001 | Michelson | |
| 6,228,085 B1 | 5/2001 | Theken et al. | |
| 6,342,074 B1 | 1/2002 | Simpson | |
| 6,413,259 B1 | 7/2002 | Lyons et al. | |
| 6,432,106 B1 | 8/2002 | Fraser | |
| 6,461,359 B1 | 10/2002 | Tribus et al. | |
| 6,524,311 B2 | 2/2003 | Gaines, Jr. | |
| 6,533,786 B1 | 3/2003 | Needham et al. | |
| 6,572,622 B1 | 6/2003 | Schafer et al. | |
| 6,579,290 B1 | 6/2003 | Hardcastle et al. | |
| 6,629,998 B1 | 10/2003 | Lin | |
| 6,645,208 B2 | 11/2003 | Apfelbaum et al. | |
| 6,656,179 B1 | 12/2003 | Schaefer et al. | |
| 6,719,794 B2 | 4/2004 | Gerber et al. | |
| 6,730,127 B2 | 5/2004 | Michelson | |
| 6,830,570 B1 | 12/2004 | Frey et al. | |
| 6,833,006 B2 | 12/2004 | Foley et al. | |
| 6,837,905 B1 | 1/2005 | Lieberman | |
| 6,884,242 B2 | 4/2005 | LeHuec et al. | |
| 6,974,480 B2 | 12/2005 | Messerli et al. | |
| 7,041,135 B2 | 5/2006 | Michelson | |
| 7,060,096 B1 | 6/2006 | Schopf et al. | |
| 7,087,055 B2 | 8/2006 | Lim et al. | |
| 7,163,561 B2 | 1/2007 | Michelson | |
| 7,232,464 B2 | 6/2007 | Mathieu et al. | |
| 7,320,708 B1 | 1/2008 | Bernstein | |
| 2002/0004683 A1 | 1/2002 | Michelson | |
| 2002/0016595 A1 | 2/2002 | Michelson | |
| 2002/0019637 A1 | 2/2002 | Frey et al. | |
| 2002/0055781 A1 | 5/2002 | Sazy | |
| 2002/0077700 A1 | 6/2002 | Varga et al. | |
| 2002/0082597 A1 | 6/2002 | Fraser | |
| 2002/0091387 A1 | 7/2002 | Hoogland | |
| 2002/0147450 A1 | 10/2002 | LeHuec et al. | |
| 2003/0028250 A1 | 2/2003 | Reiley et al. | |
| 2003/0120274 A1 | 6/2003 | Morris et al. | |
| 2003/0130661 A1 | 7/2003 | Osman | |
| 2003/0167091 A1* | 9/2003 | Scharf | 623/17.11 |
| 2003/0225409 A1 | 12/2003 | Fried et al. | |
| 2004/0127902 A1 | 7/2004 | Sukuki et al. | |
| 2004/0193269 A1 | 9/2004 | Fraser et al. | |
| 2004/0204712 A1 | 10/2004 | Kolb et al. | |
| 2004/0236333 A1 | 11/2004 | Lin | |
| 2005/0149026 A1* | 7/2005 | Butler et al. | 606/69 |
| 2005/0177236 A1 | 8/2005 | Mathieu et al. | |
| 2006/0085071 A1 | 4/2006 | Lechmann et al. | |

FOREIGN PATENT DOCUMENTS

| | | |
|---|---|---|
| EP | 1247503 | 10/2002 |
| JP | 2004500156 A | 1/2004 |
| WO | 9720526 | 6/1997 |
| WO | 9856319 | 12/1998 |
| WO | WO9858604 | 12/1998 |
| WO | 9927864 A2 | 6/1999 |
| WO | 0007527 | 2/2000 |
| WO | 0066011 A1 | 11/2000 |
| WO | 0066045 | 11/2000 |
| WO | 0135701 A2 | 1/2001 |
| WO | 0180785 | 11/2001 |
| WO | 0195837 | 12/2001 |
| WO | 0203885 A2 | 1/2002 |
| WO | WO03005938 | 1/2003 |
| WO | 2004069106 A1 | 8/2004 |
| WO | WO2004069106 | 8/2004 |

OTHER PUBLICATIONS

Langston T. Holly, M.D.; James D. Schwender, M.D.; David P. Rouben, M.D.; Kevin T. Foley, M.D., "Minimally Invasive Transforaminal Lumber Interbody Fusion: Indication Technique, and Complications", Neurosurg Focus, 2006, 7 pages, www.medscape.com, American Association of Neurological Surgeons.

Harel Deutsch, M.D.; Michale J. Musacchio, Jr., M.D., "Minimally Invasive Transforaminal Lumber Interbody Fusion With Unilateral Pedicle Screw Fixation", Neurosurg Focus, 2006, 9 pages, www.medscape.com, American Association of Neurological Surgeons.

Jonathan Tuttle, M.D.; Ahmed Shakir, M.D.; Haroon Fiaz Choudhri, M.D., "Paramedian Approach for Transforaminal Lumber Interbody Fusion With Unilateral Pedicle Screw Fixation. Technical Note and Preliminary Report on 47 Cases.", Neurosurg Focus, 2006, 9 pages, www.medscape.com, American Association of Neurological Surgeons.

* cited by examiner

LATERAL MOUNT IMPLANT DEVICE

RELATED PATENT APPLICATION

This application claims the benefit of U.S. Provisional Patent Application No. 60/782,795 filed Mar. 16, 2006, and claims the benefit of and is a continuation in part application of U.S. patent application Ser. No. 11/620,255 filed Jan. 5, 2007, now U.S. Pat. No. 8,100,976, and U.S. patent application Ser. No. 11/248,651 filed Oct. 12, 2005, now U.S. Pat. No. 7,985,255, both of which claim benefit of and are continuations-in-part applications of U.S. patent application Ser. No. 10/419,652 filed Apr. 21, 2003, now U.S. Pat. No. 6,984,234, the contents of all of which are incorporated herein by reference in their entirety.

BACKGROUND OF THE INVENTION

1. Field of the Invention

The present invention relates generally to devices for the fixation and support of vertebrae. In particular, the present invention relates to an implant device having a lateral mounting portion that provides and controls limited movement between the vertebrae during fusion.

2. Background of the Invention

The spinal column of vertebrates provides support to bear weight and protection to the delicate spinal cord and spinal nerves. The spinal column includes a series of vertebrae stacked on top of each other. There are typically seven cervical (neck), twelve thoracic (chest), and five lumbar (low back) segments. Each vertebra has a cylindrical shaped vertebral body in the anterior portion of the spine with an arch of bone to the posterior, which covers the neural structures. Between each vertebral body is an intervertebral disk, a cartilaginous cushion to help absorb impact and dampen compressive forces on the spine. To the posterior, the laminar arch covers the neural structures of the spinal cord and nerves for protection. At the junction of the arch and anterior vertebral body are articulations to allow movement of the spine.

Various types of problems can affect the structure and function of the spinal column. These can be based on degenerative conditions of the intervertebral disk or the articulating joints, traumatic disruption of the disk, bone or ligaments supporting the spine, tumor or infection. In addition congenital or acquired deformities can cause abnormal angulation or slippage of the spine. Anterior slippage (spondylolisthesis) of one vertebral body on another can cause compression of the spinal cord or nerves. Patients who suffer from one of more of these conditions often experience extreme and debilitating pain, and can sustain permanent neurological damage if the conditions are not treated appropriately.

One technique of treating these disorders is known as surgical arthrodesis of the spine. This can be accomplished by removing the intervertebral disk and replacing it with bone and immobilizing the spine to allow the eventual fusion or growth of the bone across the disk space to connect the adjoining vertebral bodies together. The stabilization of the vertebra to allow fusion is often assisted by a surgically implanted device to hold the vertebral bodies in proper alignment and allow the bone to heal, much like placing a cast on a fractured bone. Such techniques have been effectively used to treat the above-described conditions and in most cases are effective at reducing the patient's pain and preventing neurological loss of function. However, there are disadvantages to some present stabilization devices.

The spinal fixation device needs to allow partial sharing of the weight of the vertebral bodies across the bone graft site. Bone will not heal if it is stress shielded from all weight bearing. The fixation device needs to allow for this weight sharing along with the micromotion that happens during weight sharing until the fusion is complete, often for a period of three to six months or longer, without breakage. The device must be strong enough to resist collapsing forces or abnormal angulation during the healing of the bone. Loss of alignment during the healing phase can cause a poor outcome for the patient. The device must be secure in its attachment to the spine to prevent migration of the implant or backout of the screws from the bone, which could result in damage to the structures surrounding the spine, resulting in severe and potentially life threatening complications. The device must be safely and consistently implanted without damage to the patient.

Several types of anterior spinal fixation devices are in use currently. Problems have resulted from over-rigid fixation and stress shielding, resulting in nonunion of the fusion material, chronic micromotion during healing resulting in stress fracture of the fixation device at either the screw or the plate, insufficient locking of the screws to the plate resulting in screw backout, or inadequate fixation strength and resultant collapse of the graft and angulation of the spine.

For some areas of the spinal column surgical implantation may be difficult from certain directions. For example, surgical implantation in the thoracic and lumbar segments from an anterior side of the spine also requires addressing issues concerning internal organs that are located on the anterior side of the spine.

BRIEF SUMMARY OF THE INVENTION

The following presents a simplified summary of the invention in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

In accordance with an aspect of the present invention, an implant device for the spine is provided. The implant device includes a base member configured to interface with two adjacent vertebrae. The base member includes a lateral mounting portion configured to accommodate securing or fixing the implant device to a lateral side of at least one of the vertebrae that the implant device interfaces. The base member can include an elongated side portion that extends from a side of the lateral mounting portion of the base member such that the elongated side portion extends between the at least two vertebrae. The elongated side portion has at least one interface member extending from a surface thereon. The at least one interface member is configured to provide controlled subsidence of the implant device into at least one vertebra. The implant device further includes a plurality of bone fasteners extending through apertures provided in the lateral mounting portion of the base member. It is to be appreciated that the design of the implant device described herein is suitable for insertion through a posterior lateral or lateral opening that exposes a lateral side of the vertebrae to which the implant device is mounted.

In accordance with another aspect of the present invention, an implant device for the spine is provided. The implant device includes a base member having a lateral mounting portion to accommodate fixation of the implant device to a lateral side of at least one vertebra. The base member further includes an elongated side portion extending from a side of the lateral mounting portion in a direction towards the at least one vertebra the implant device is to be mounted to, wherein the elongated side portion interfaces with the at least one vertebra. At least one interface member extends from a surface of the elongated side portion, wherein the at least one interface member is configured to provide controlled subsidence of the implant device into the at least one vertebra. The implant device further includes a plurality of bone fasteners extending through apertures provided in the lateral mounting portion of the base member. The implant device can also include a restraining means, such as a plate or cover, for restricting movement of at least one of the bone fasteners extending through apertures provided in the lateral mounting portion of the base member.

The following description and the annexed drawings set forth in detail certain illustrative aspects of the invention. These aspects are indicative, however, of but a few of the various ways in which the principles of the invention may be employed and the present invention is intended to include all such aspects and their equivalents. Other objects, advantages and novel features of the invention will become apparent from the following detailed description of the invention when considered in conjunction with the drawings.

BRIEF DESCRIPTION OF THE DRAWINGS

The foregoing and other features and advantages of the present invention will become apparent to those skilled in the art to which the present invention relates upon reading the following description with reference to the accompanying drawings.

DESCRIPTION OF EXAMPLE EMBODIMENTS

Figure 1:
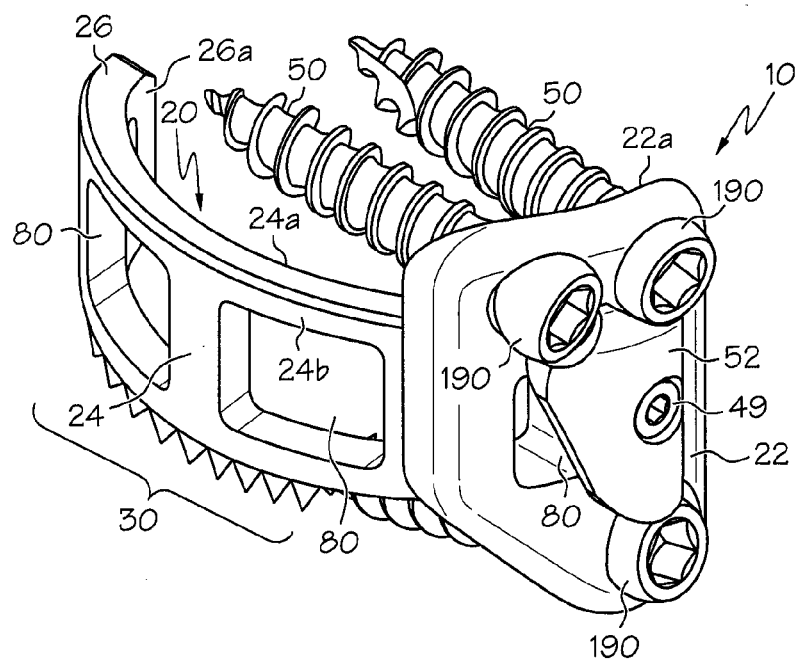
FIG. 1 is an angled lateral side perspective view of an implant device in accordance with an aspect of the present invention.

The present invention relates to an implant device that provides and controls limited movement between vertebrae during fusion. The present invention will now be described with reference to the drawings, wherein like reference numerals are used to refer to like elements throughout. It is to be appreciated that the various drawings are not necessarily drawn to scale from one figure to another nor inside a given figure, and in particular that the size of the components are arbitrarily drawn for facilitating the understanding of the drawings. In the following description, for purposes of explanation, numerous specific details are set forth in order to provide a thorough understanding of the present invention. It may be evident, however, that the present invention can be practiced without these specific details. Additionally, other embodiments of the invention are possible and the invention is capable of being practiced and carried out in ways other than as described. The terminology and phraseology used in describing the invention is employed for the purpose of promoting an understanding of the invention and should not be taken as limiting.

The implant device 10, any portions or combination of portions thereof, described and illustrated herein, can be constructed from radiopaque or radiolucent materials, or combinations of such materials. Radiolucent materials can include, but are not limited to, polymers, carbon composites, fiber-reinforced polymers, plastics, combinations thereof and the like. One example of a radiolucent material that can be used with the present invention is PEEK-OPTIMA® polymer supplied by Invibio Inc., Greenville, S.C. The PEEK-OPTIMA® polymer is a polyaromatic semicrystalline thermoplastic known generically as polyetheretherketone. The PEEK-OPTIMA® polymer is a biocompatible and inert material. Radiopaque materials are traditionally used to construct devices for use in the medical device industry. Radiopaque materials can include, but are not limited to, metal, aluminum, stainless steel, titanium, titanium alloys, cobalt chrome alloys, combinations thereof and the like.

Radiolucent materials can be utilized to facilitate radiographic evaluation of fusion material or vertebrae near the implant device 10. For example, radiolucent materials permit x-rays to pass through the implant device 10 or components thereof so that developed x-ray pictures provide more visibility of the fusion material and vertebrae without significant interference, such as imaging artifacts, caused by the device 10. Radiolucent materials can enable clear visualization through imaging techniques such as x-ray and computer tomography (CT), whereas traditional radiopaque metallic or alloy materials can generate imaging artifacts or scatter that may prevent a comprehensive inspection of the surrounding tissue, vertebra and fusion material. In order to address the general disadvantage that some radiolucent materials lack the strength of radiopaque materials, design modifications may be required to provide adequate structural integrity and durability to the implant device 10. For example, the thickness of portions of the implant device 10 subject to stress and strain can be increased in order to add support and structural integrity. Thicker or bulkier construction can mitigate the stresses of vertebra migration and toggling of the bone fasteners that may cause the implant device 10 to bend, crack or otherwise be damaged while in use.

Referring initially to FIGS. 1 through 4, an implant device 10 suitable for lateral or postero-lateral insertion is illustrated in accordance with an aspect of the present invention. The implant device 10 is configured to interact with two bone vertebrae, as similarly shown in FIGS. 12 through 14. For example, the implant device can fix and secure adjacent vertebrae that have had cartilaginous disc between the vertebrae replaced with fusion material that promotes the fusion of the vertebrae, such as a graft of bone tissue. It is to be appreciated that one aspect that is addressed by the present invention is load sharing with a graft.

Figure 12:
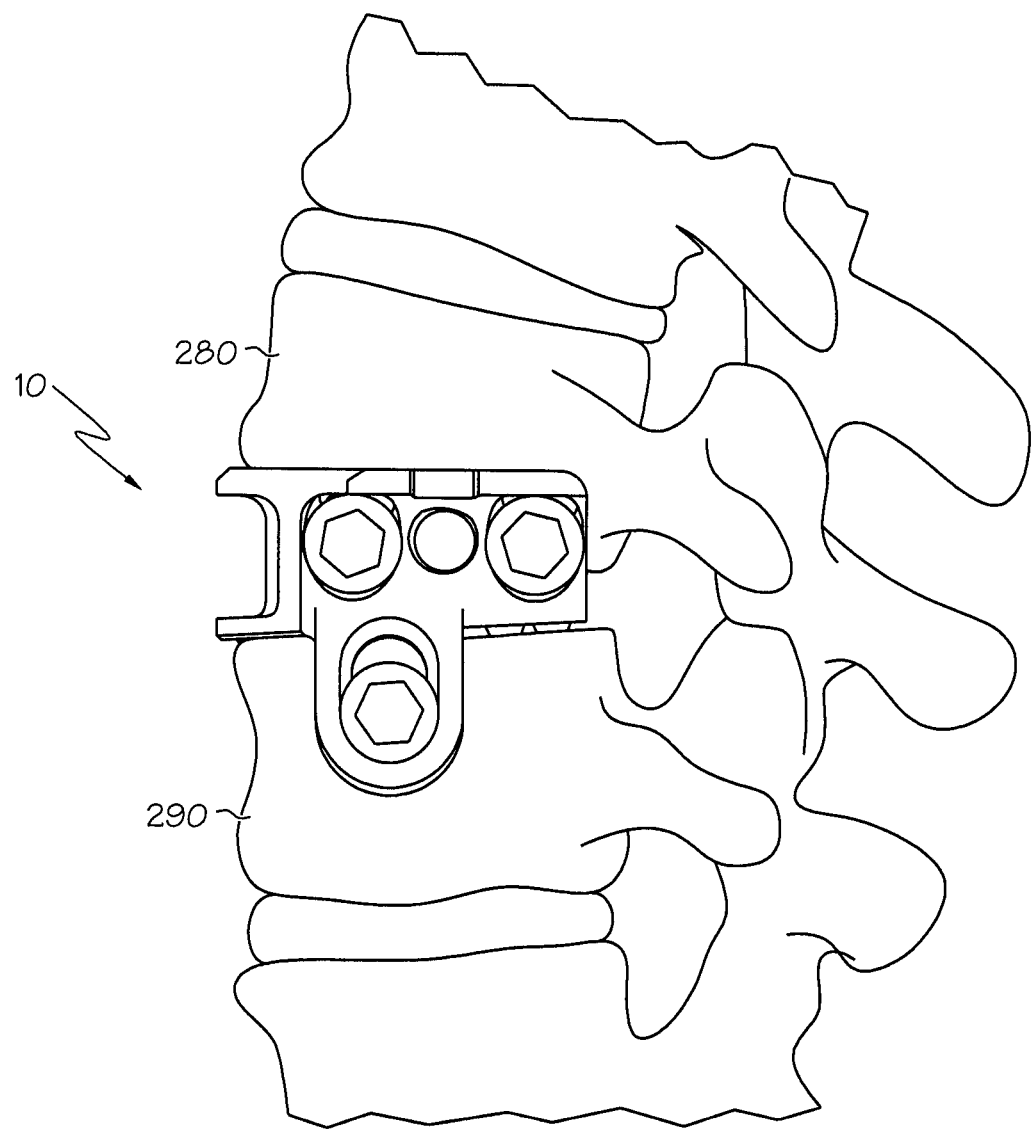
FIG. 12 is a lateral side view of an implant device positioned between two vertebrae in accordance with an aspect of the present invention.

The implant device 10 illustrated in FIGS. 1 through 4 includes a base member 20 having a lateral mounting portion 22, an elongated side portion 24 and a back portion 26. In the present embodiment, the lateral mounting portion 22, elongated side portion 24 and back portion 26 are contiguous and unitary. For example, FIG. 1 illustrates that the lateral mounting portion 22 is contiguous with one end of the elongated side portion 24 whereas the other end of the elongated side portion 24 is contiguous with the back portion 26. In use, the inner surface 24a of the elongated side portion 24 faces towards the spinal column (i.e. the posterior face) whereas the outer surface 24b of the elongated side portion 24 faces away from the spinal column (i.e. the anterior face). Thus, the elongated side portion 24 has a posterior face and an anterior face relative to the vertebrae of the spine. The lateral mounting portion 22 is illustrated as being suitable for mounting or securing the device 10 to the left lateral side of a patient's spine. An example of the implant device 10 mounted to the left lateral side of a spinal column is illustrated in FIG. 12. It is to be appreciated in the description of the implant device 10 that the lateral mounting portion and back portion can be transposed in order to accommodate mounting of the device 10 on the right side of a patient's spine. In this alternative configuration, the back portion would be provided on the left side of the spinal column, if desired. As shown, the base member 20 is generally curved such that the elongated side portion 24 forms an arch or curvature that suitably corresponds to the cylindrical shape of a vertebral body of a spine. The back portion 26 of the base member 20 forms a lip or end portion and is curved so the inner face 26a of the back portion 26 substantially opposes the inner face 22a of the lateral mounting portion 22. The back portion 26 of the base member 20 is generally shorter than the lateral mounting portion 22. The shortened back portion 26 of the base member 20 facilitates the rotation of the implant device 10 around fusion material that can be positioned between two adjacent vertebrae through a posterior lateral or lateral opening exposing a lateral side of the vertebrae. The shortened back portion 26 advantageously allows the device 10 to be minimally extended or pushed in the anterior direction of the spine in order to insert the device 10 between two adjacent vertebrae. Otherwise, if the back portion 26 were greater than or substantially the same length as the lateral mounting portion 22, the device 10 would generally be pushed farther into the anterior portion of the patient's body during insertion to facilitate positioning the device around a graft located between vertebrae. In this case, disrupting or puncturing an internal organ would generally be increased. The fusion material could alternatively be inserted or located between vertebrae after insertion of the device 10. As used herein, it is to be appreciated that fusion material can include, but is not limited to, bone chips, bone paste, bone graft, combinations thereof and the like.

The lateral mounting portion 22 of the base member 20 includes at least one aperture configured to receive a bone fastener 50 extending therethrough. The aperture can be of any shape or size such as a round hole or elongated slot. The bone fastener 50 can include a bone screw, which is used for securing the implant device 10 to adjacent vertebrae, and in particular to a lateral peripheral side of at least one vertebra. The bone fastener 50 can be made of any suitable material, such as titanium or a titanium alloy, a radiolucent material, a radiopaque material, or combinations thereof. If a plurality of bone fasteners is used, the fasteners can all have the same shape, such as the fasteners 50 shown in FIGS. 1 and 2. In the representative Figures, the bone fasteners 50 each have a radiused head 190. As used herein, the term "radiused head" means that the lower portion of the bone fastener head, i.e., the portion that is nearest the shank, is generally rounded to thereby permit the bone fasteners to toggle, pivot or slide within their respective apertures.

In another embodiment, the bone fasteners 50 configured to pass through the apertures in the lateral mounting portion 22 can have pointed ends which include a cutting section such as a flute on the tip. The pointed end and cutting flute allow the fastener to be self-drilling or self-tapping. Thus, the use of a bone fastener 50 having a self-drilling or self-tapping tip makes the use of a drill or center punch optional. In use, the bone fasteners 50 can be inserted through apertures in the lateral mounting portion 22 into corresponding vertebrae via a flex driver or the like. Alternatively, any other suitable method of securing the implant device 10 to the vertebrae can be employed and is contemplated as falling with the scope of the present invention.

Figure 3:
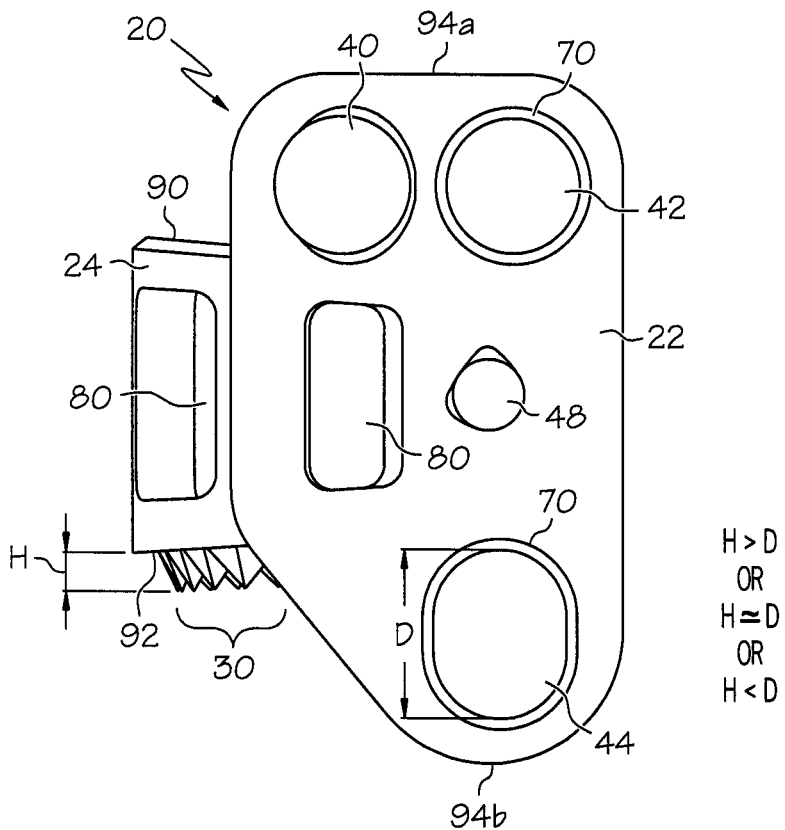
FIG. 3 is a lateral side view of the implant device of FIG. 1.

FIG. 3 illustrates that the lateral mounting portion 22 can have at least three apertures 40, 42, 44. Apertures 40 and 42 of FIG. 3 are positioned in the segment towards the top surface 94a of the lateral mounting portion 22 and are configured as round holes. The apertures 40 and 42 can have a seat 70 on which the retaining portion of a respective bone fastener head rests. Each seat 70 has a generally concave spherical shape and the surface of the retaining portion of the bone fastener 50 in contact with the seat 70 has a complementary convex spherical configuration. Consequently, the bone fasteners 50 are free to pivot on the seats 70 during controlled subsidence. Aperture 44 is positioned in the segment towards the bottom surface 94b of the lateral mounting portion 22. Aperture 44 is configured as an elongated slot and can accommodate toggling and/or sliding of a bone fastener 50 along the elongation length of the slot 44, which is labeled distance (D) in FIG. 3. In use, as two adjacent vertebrae, to which the implant device 10 is fixed, collapse or settle and move toward each other, the bone fastener 50 extending through aperture 44 will slide or travel within the slot and move with the vertebra into which it extends in a direction toward the other adjacent vertebra. As shown, the lateral mounting portion 22 can further include a mounting hole 48 for receiving a restraining means for preventing the backing out of at least one bone fastener from a vertebra. The restraining means may be any means for securely covering at least a portion of at least one bone fastener 50 or the head 190 of the bone fastener 50 so that the bone fastener 50 is prevented from backing out of a vertebra once screwed in. For example, the restraining means can be a cover or plate. FIG. 1 illustrates one embodiment of a restraining plate 52 that can be secured to the lateral mounting portion 22 by a screw or other conventional fastener configured to pass through the mounting hole 49 in the plate 52 that is in register with the mounting hole 48 of the lateral mounting portion 22. The top segment of the restraining plate 52 covers a portion of the bone fasteners 50 extending through apertures 40 and 42 of the lateral mounting portion 22 to prevent back out while simultaneously allowing the fasteners 50 to toggle or pivot in the apertures 40, 42. The bottom segment of the restraining plate 52 configured to cover at least a portion of the bone fastener 50 extending through elongated slot 44 can be designed to permit that bone fastener 50 to slide and toggle within the slot 44. For instance, the bottom segment of the restraining plate 52 can have a notch that corresponds to the head 190 of the bone fastener 50 so the bone fastener 50 is free to move or toggle. Additionally, it is to be appreciated that any other suitable bone fastener restraining means, other than the restraining plate 52 of FIG. 1, can be used in connection with the present invention. For example, the restraining means can include multiple restraining plates that cover different bone fasteners. Alternatively, the restraining means can include one or more screws with heads that overlap at least a portion of one or more bone fasteners to thereby prevent the bone fasteners from backing out. Alternative example embodiments of restraining means and the way the embodiments interface with the bone fasteners are illustrated and described in U.S. patent application Ser. No. 11/620,255, which is incorporated herein by reference in its entirety.

Figure 4:
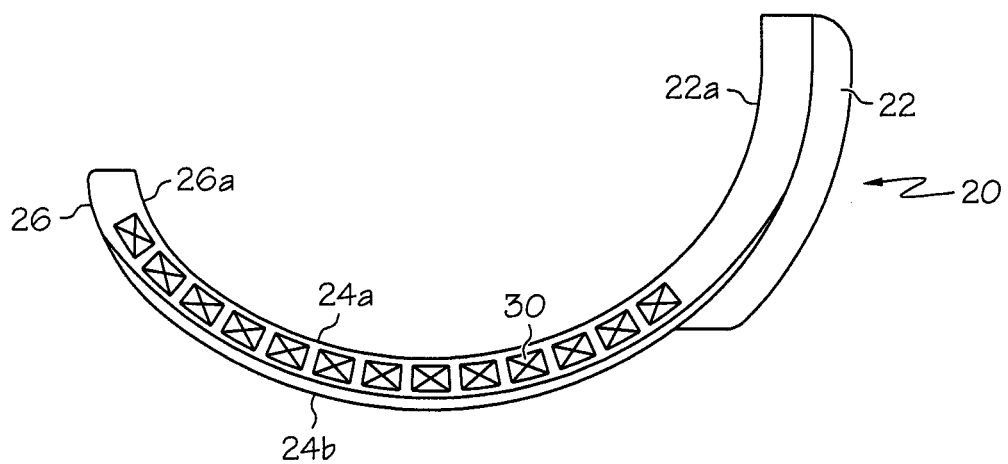
FIG. 4 is a top view of an implant device in accordance with an aspect of the present invention.

The base member 20 can also include at least one protrusion or interface member 30 extending from a surface of the base member 20. As shown in FIGS. 1 and 3, a plurality of interface members 30 can extend from the bottom surface 92 of the elongated side portion 24. FIG. 4 illustrates a plurality of interface members 30 extending from the top surface 90 of the elongated side portion 24. Although not specifically shown, the interface members 30 can extend from more than one surface of the elongated side portion 24, such as from both the top surface 90 and the bottom surface 92 of the elongated side portion 24 in order to provide two controlled subsidence interfaces between the implant device 10 and adjacent vertebrae. The interface members 30 are configured to contact at least one surface of a vertebra to provide subsidence control for the implant device 10. Accordingly, when coupled with the vertebrae, the interface members 30 extend from the elongated side portion 24 in a direction that is aligned with an elongate direction of the spine. As will be explained in further detail below, controlled subsidence relates to the resistance to subsidence and total amount of subsidence. The interface members 30 can include, but are not limited to, teeth, knife-edges, spikes, posts, pegs, or combinations thereof.

The base member 20 is configured such that when first inserted between two adjacent vertebrae, the interface members 30 contact a surface of at least one of the vertebrae. The interface members are thus configured to provide progressive penetration into a vertebra over a period of time. The sharp or pointed ends of the interface members 30 are suitably designed to substantially immediately penetration into a vertebra. The implant device 10 gradually subsides as the vertebrae and bone graft fuse to share in the weight bearing during settling of the bone or vertebral bodies. Specifically, as the vertebrae move toward each other during settling, the interface members 30 will penetrate the vertebrae with increased resistance to subsidence. The subsidence profile, which is a relationship between an applied load and an amount of settling the implant device 10 experiences when secured to the vertebrae, is dependent on the configuration, shape, or height (H) of the interface members 30. For example, the interface members 30 can readily penetrate into a vertebra initially and then slow down as more of the interface member cross section embeds. The height (H) of the interface members 30 correspond to the depth of penetration into a vertebra. Generally, when the implant device 10 has subsided to a point where the interface members are fully embedded in the bone, the applied load will be distributed across the entire surface of the implant device 10 and subsidence resistance will increase. The controlled subsidence relationship between the interface members 30 and the at least one corresponding vertebra that the members 30 extend into is described in U.S. patent application Ser. No. 11/248,651, which is incorporated herein by reference in its entirety.

Figure 2:
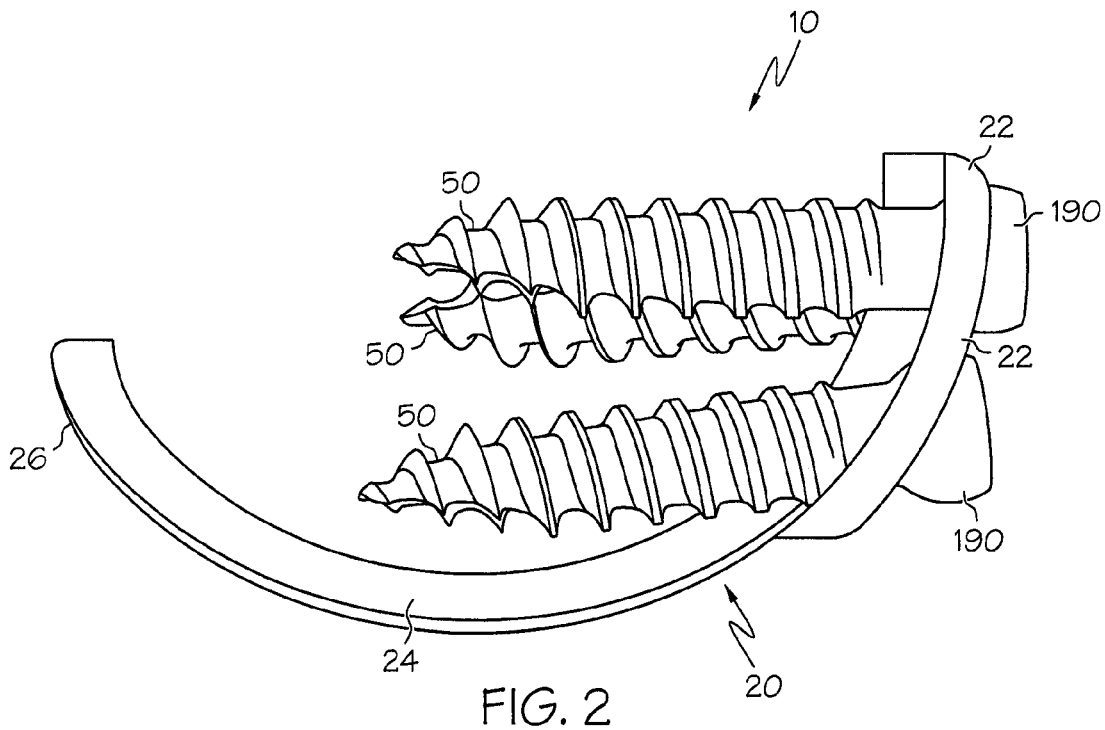
FIG. 2 is a top view of the implant device of FIG. 1.

As illustrated in FIGS. 1 through 3, the apertures 40, 42, 44 extend substantially straight through the lateral mounting portion 22 such that the apertures are not angled with respect to the face of the lateral mounting portion 22. The bone fasteners 50 can however be inserted through the apertures 40, 42, 44 such that the tips of the fasteners 50 are angled towards each other as the fasteners 50 penetrate into a vertebra. The radiused head 190 of the bone fastener 50 resting against the aperture seat 70 allows the fastener 50 to pivot, for example from side to side, to accommodate a desirable entry direction into a vertebra. Because the lateral mounting portion 22 has some curvature corresponding to the shape of the elongated side portion 24, the pivoting motion of the bone fastener 50 described above mitigates having to insert a bone fastener 50 at an undesirable entry angle into a vertebra.

As mentioned above, the height (H) of the interface members 30 relates to the depth of penetration of the interface members into the vertebra. The height (H) can also have an interrelationship with other relative movements that are associated with the implant device 10. For example, penetration of the interface members 30 into a vertebra can be coordinated with the pivoting and/or sliding of one or more bone fasteners relative to their respective round holes 40, 42 and/or slot 44 for controlled subsidence. As shown in FIG. 3, a bone fastener 50 associated with slot 44 can have a travel or slide distance (D) along the elongated length of the slot. As will be appreciated below, the elongation length of the slot 44 directly relates to the travel distance (D) labeled in the Figures. The interface member 30 height (H) can be equal to the distance (D) such that when the members 30 reach a fully-embedded state, the bone fastener 50 will slide along distance (D) and reach the end of the slot 44. Thus, the respective bone fastener is located within the slot 44 so the fastener travel will match the penetration subsidence of the interface members into a vertebra. Alternatively, other examples regarding relative dimensioning are contemplated. Other examples can include relative sliding travel of the fastener 50 within the slot 44 to end before the interface members 30 reach a fully-embedded state and relative sliding travel of the fastener 50 within the slot 44 to still be permitted after the interface members 30 reach a fully-embedded state. Such examples can generally be characterized by considering the interface member height (H) to be greater than the travel distance (D) and by considering such height (H) to be less than such distance (D), respectively. Also, placement and sliding travel are possible variables. For example, the respective bone fastener 50 can be placed to reach an end of the elongated slot 44 and then toggle in the slot 44 to permit the interface members 30 to further penetrate into the vertebra.

In yet another example (not shown), as mentioned above, the interface members 30 can extend from the top surface 90 and the bottom surface 92 of the elongated side portion 24. In this case, the apertures located in the lateral mounting portion 22 can be in the form of elongated slots having an elongation length, as similarly described with regard to aperture 44 of FIG. 3, in order to provide relative movement of the bone fasteners extending through the elongated slots during controlled subsidence. In this example, the elongated slot or slots near the top segment of the lateral mounting portion 22 correspond to the interface members 30 extending from the top surface 90 of the elongated side portion 24 and the elongated slot or slots near the bottom segment would correspond to the interface members 30 extending from the bottom surface of the elongated side portion 24. Thus, the elongation length of the slots can match the height (H) of their respective interface members 30 or alternatively be less than or more than the height (H) of the interface members 30 in order to provide the desired subsidence profile.

In any case, it is to be appreciated that one or more slots, such as aperture 44, can be positioned in any desirable location within the lateral mounting portion 22. For example, the aperture round holes 40, 42 can be inverted with the aperture slot 44 such that there are two aperture slots located towards the top surface 94*a* of the lateral mounting portion 22 and one aperture round hole located towards the bottom surface 94*b* of the lateral mounting portion 22. In yet another example, the lateral mounting portion 22 can have apertures only in the form of slots or apertures only in the form of round holes. In the case the apertures in the lateral mounting portion 22 are all round holes, no relative sliding movement may occur between the bone fasteners 50 and the base member 20 during the controlled subsidence.

Another aspect that can affect the subsidence profile is the height (H) or combination of heights of the interface members 30. That is, the interface members 30 can be of any height or combination of heights. For instance, if a plurality of interface members 30 extend from a surface of the base member 20, such as the bottom surface 92 of the elongated side portion 24, each interface member 30 can be of equal heights or substantially taller or shorter than other interface members 30. Although not shown, if interface members 30 extend from the top surface and the bottom surface of the base member 20, the height (H) of the interface members 30 extending from the top surface may be greater, about the same, or less than height (H) of the interface members 30 extending from the bottom surface.

The implant device 10, as shown in FIGS. 1 through 4 can also include a plurality of pathways for vascularization or fusion windows 80 spaced along the base member 20. The windows can be located in the lateral mounting portion 22, elongated side portion 24 or back portion 26 of the base member 20. The fusion windows 80 tend to facilitate visualization of the fusion material on x-rays and bone growth therethrough when the implant device 10 is positioned between two vertebrae.

Figure 5:
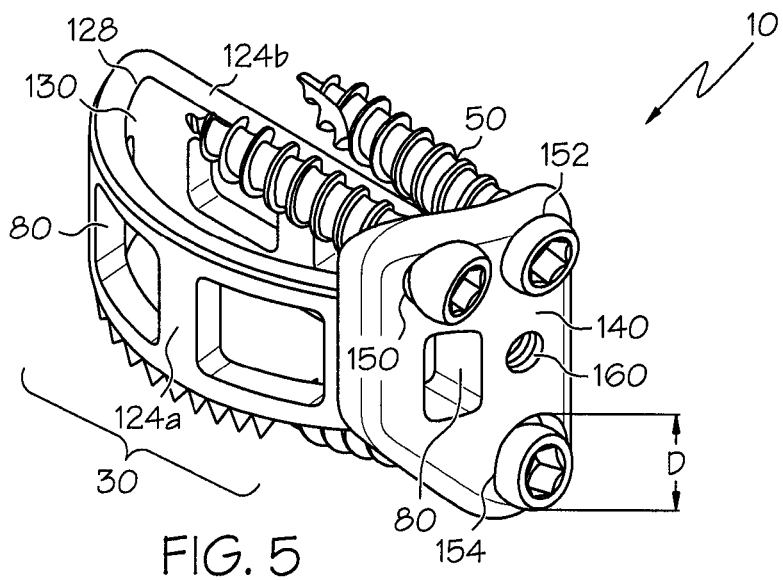
FIG. 5 is an angled lateral side perspective view of an implant device in accordance with an aspect of the present invention.
Figure 6:
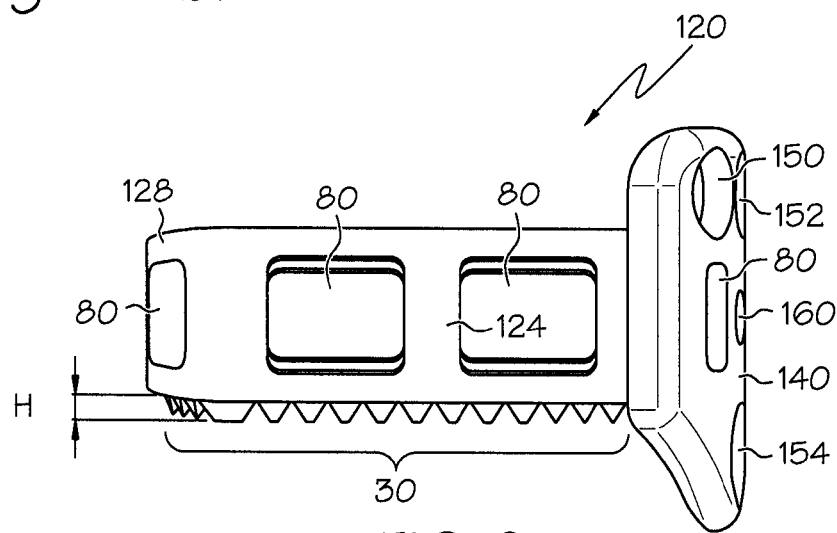
FIG. 6 is an anterior view of the implant device of FIG. 5.
Figure 7:
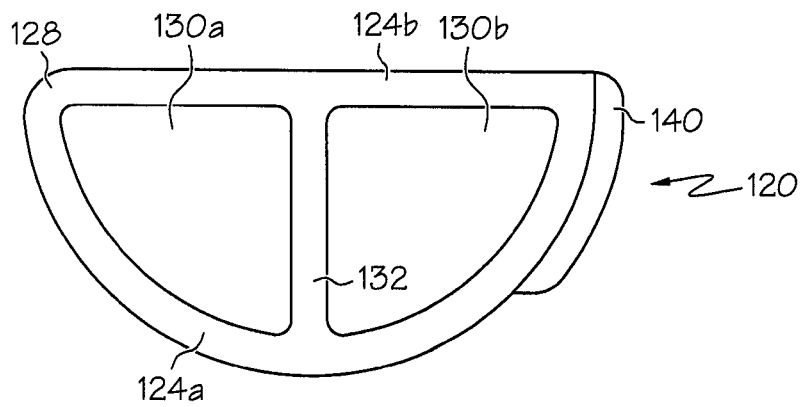
FIG. 7 is a top view of an implant device in accordance with an aspect of the present invention.

In another embodiment, as shown in FIGS. 5 through 7, the implant device 10 configured for lateral or postero-lateral insertion can have a base member 120 including an elongated side portion 124 that forms an enclosed loop or peripherally-surrounded bone chamber 130 for receiving or holding fusion material. As shown, the chamber 130 is peripherally-surrounded, but not fully enclosed, such that vertebrae residing above and below the chamber 130 can be in contact with fusion material located in the chamber 130. It is to be appreciated, and for the description purposes of the present invention herein, the peripherally-surrounded chamber 130 can be positioned at any angle in order to accommodate the orientation of vertebrae to be fused together. In any case, the chamber 130 can mitigate lateral shift of the fusion material and control subsidence of adjacent vertebrae as they set during fusion. The elongated side portion 124 can form the peripherally-surrounded chamber 130 to be of any shape or size to accommodate adjacent vertebrae of various shapes, sizes and positions. The chamber 130 of the implant device 10 creates a one-piece fusion material housing that substantially reduces the need for other devices that may be necessary to fuse multiple vertebrae together. The peripherally-surrounded chamber 130 adequately houses fusion material that would generally be supported by a cage design implant. In this case, a plate would generally also be needed to keep the vertebrae and the cage in the desired location. The implant device 10 described herein significantly reduces the cost associated with multiple-device fusion methods such as those associated with the above cage and plate combination devices.

The peripherally-surrounded chamber 130 of the present embodiment is desirably designed to have an outer periphery that coincides with a portion of the outer diameter of the cortex or adjacent vertebrae, such as the convex anterior face of spinal vertebrae. As shown, the peripherally-surrounded chamber 130 has an elongated and generally narrow peripheral shape to accommodate easier insertion into a patient. In other words, the device 10 of the present embodiment is adapted for a lateral or postero-lateral insertion such that the narrow elongated shape of the chamber 130 reduces the anterior distance the device 10 must be pushed in order to clear the fusion material, which can be located between two vertebrae. Alternatively, the device 10 can be loaded with load fusion material such as bone paste or bone chips prior to insertion between adjacent vertebrae (e.g., vertebrae).

The elongated side portion 124 of the base member 120 forms a chamber 130, as shown in FIGS. 5 through 7, that is vertically open. The elongated side portion 24 has two side walls 124*a*, 124*b* (i.e. and anterior and posterior side, respectively). The anterior side wall 124*a* forms an arch or curvature that suitably corresponds to the cylindrical shape of a vertebral body of a spine. The posterior side wall 124*b* is substantially straight. Thus, the anterior wall 124*a* and the posterior wall 124*b* are not parallel with one another as shown. The posterior wall 124*b* has distal ends (one distal end being against the lateral mounting portion 140) that are contiguous with the distal ends of the anterior wall 124*a*. For example, the distal ends of the posterior wall 124*b* and the anterior wall 124*a* being away from the lateral mounting portion 140 are contiguous and form a lateral end point 128 of the chamber 130. The lateral end point 128 is located opposite the lateral mounting portion 140 and can be rounded or blunt. The lateral mounting portion 140 forms a segment of the peripherally-surrounded chamber 130 and can be curved or rounded to correspond with the curved shape of the anterior wall 124*a* of the chamber 130. The anterior and posterior walls 124*a*, 124*b* and the lateral mounting portion 140 can have fusion windows 80 as similarly described with regard to FIG. 1. The lateral mounting portion 140 of the device 10 can have at least one aperture in the form of a round hole or elongated slot and an optional mounting hole 160 for receiving a restraining means as described above with regard to FIGS. 1 through 4. In the case that the lateral mounting portion 140 has more than one aperture, any combination and arrangement of round holes and/or elongated slots is contemplated. It is also contemplated that the apertures can have an interrelationship with the height (H) of the interface members 30 and/or other relative movements that are associated with the implant device 10 as described with regard to FIGS. 1 through 4. FIG. 6 illustrates that segments of the lateral mounting portion 140 extend vertically above and below the top surface and bottom surface of the curved side walls 124*a*, 124*b*. The segment extending above the top surface of the walls has two apertures 150, 152 in the form of round holes. The segment extending below the bottom surface of the walls has one aperture in the form of an elongated slot 154. Thus, bone fasteners 50 extending through apertures 150, 152, 154 in the lateral mounting portion 140 can penetrate into vertebrae above and below the peripherally-surrounded bone chamber 130. As shown, apertures 150, 152, 154 extend substantially straight through the lateral mounting portion 140. In use, the bone fasteners 50 can be inserted through the apertures so that the tips of the fasteners 50 are angled towards each other.

In the present embodiment, subsidence is controlled, as described above, by the interface members 30 that extend from at least one surface of the base member 120. FIG. 6 illustrates interface members 30 extending from the bottom surface of the elongated side portion 124 in a direction that is aligned with an elongate direction of the spine. Although not shown, the interface members 30 can alternatively extend from a top surface of the base member 120 or from both the top and bottom surfaces of the base member 120.

The peripherally-surrounded bone chamber 130 illustrated in FIGS. 5 through 7 can also be divided into multiple interior compartments by interior members (not shown in FIGS. 5 and 6). The number of interior compartments desired can be achieved by utilizing one or more interior members that divide the chamber 130. For example, an interior member can extend between the opposing inner surface faces, which can be substantially flat, of the chamber 130 such that the chamber 130 is divided into two compartments. The interior compartments can each hold or house fusion material to be placed between two adjacent vertebrae. The use of interior members in the peripherally-surrounded chamber 130 can add overall support and strength to the implant device 10.

FIG. 7 illustrates a bone chamber 130 having two interior compartments 130a, 130b suitable for holding fusion material. Interior member 132 extends between and connects to the posterior wall 124b and anterior wall 124a of the peripherally-surrounded bone chamber 130 and divides the chamber 130 into two compartments 130a, 130b. As shown, the interior member 132 extends from the substantially flat inner face surface of the posterior wall 124b and connects to the opposing inner face surface of the anterior wall 124a.

Figure 8:
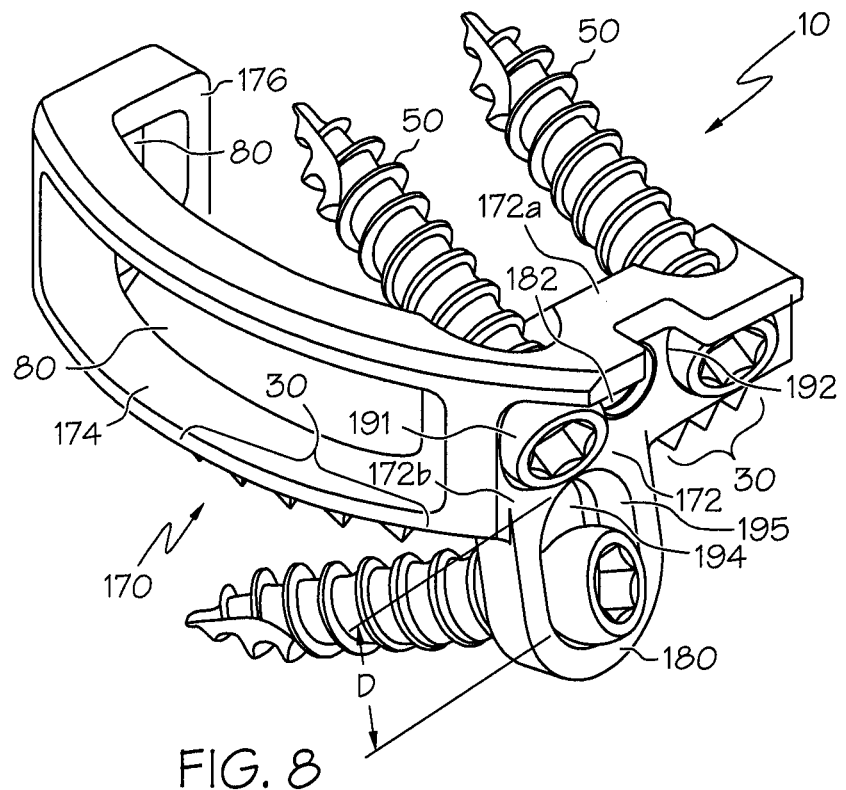
FIG. 8 is an angled lateral side perspective view of an implant device in accordance with an aspect of the present invention.

Turning to FIG. 8, another embodiment of the implant device 10 is shown. The implant device 10 is configured for lateral or postero-lateral insertion and includes a base member 170 having a lateral mounting portion 172, an elongated side portion 174 and a back portion 176. In the present embodiment, the lateral mounting portion 172, elongated side portion 174 and back portion 176 are contiguous and unitary. As similarly described above with regard to FIGS. 1 through 4, the base member 170 is generally curved or arched such that the elongated side portion 174 generally corresponds to the cylindrical shape of a vertebral body of a spine. The back portion 176 also similarly forms a lip or end portion and is curved so the back portion 176 substantially opposes the lateral mounting portion 172. In other words, the back portion 176 is substantially parallel with the lateral mounting portion 172. It is advantageous that the back portion 176 is generally shorter than the lateral mounting portion 172 in order to facilitate the rotation of the implant device 10 around fusion material positioned between two adjacent vertebrae. For example, the shortened back portion 176 allows the device 10 to be inserted between to spinal vertebrae without being significantly pushed in the anterior direction of the spine.

As described above, the interface members 30 can extend from at least one surface (i.e. bottom, top, side or combinations thereof of the base member 170 to provide subsidence control. As depicted in FIG. 8, the interface members 30 extend from the bottom surface of the base member 170. It is also contemplated that the interrelationship between the height (H) of the interface members 30, the slide distance (D) of an aperture in the lateral mounting portion 170 (not shown) and other relative movements that are associated with the implant device 10 is similar to that described with respect to FIGS. 1 through 4.

The lateral mounting portion 172 of the present embodiment can have at least one or more apertures extending therethrough configured as round holes, elongated slots, combinations thereof and the like and an optional mounting hole 198 for receiving a restraining means as described above. As shown, apertures 191, 192 are in the form of angled round holes to allow bone fasteners 50 extending therethrough to penetrate vertebrae at an angle. For instance, angled round hole 191 extends through a corner that joins a top surface 172a of the lateral mounting portion 172 to a back surface 172b of the lateral mounting portion 172, as best shown in FIG. 8. As a result, a bone fastener 50 extending through angled round hole 191 can enter a vertebra at an angle. The apertures 191, 192 of the front mounting portion 172 are sufficiently large to allow a portion of a respective bone fastener 50 to pass therethrough but not large enough to allow a retaining portion of the bone fastener through, such as the head. Further, each aperture has a seat 195 on which the retaining portion of a respective bone fastener rests such that the fastener can pivot or toggle. The lateral mounting portion 172 can also include an optional mounting round hole 182 for receiving a restraining means.

Figure 9:
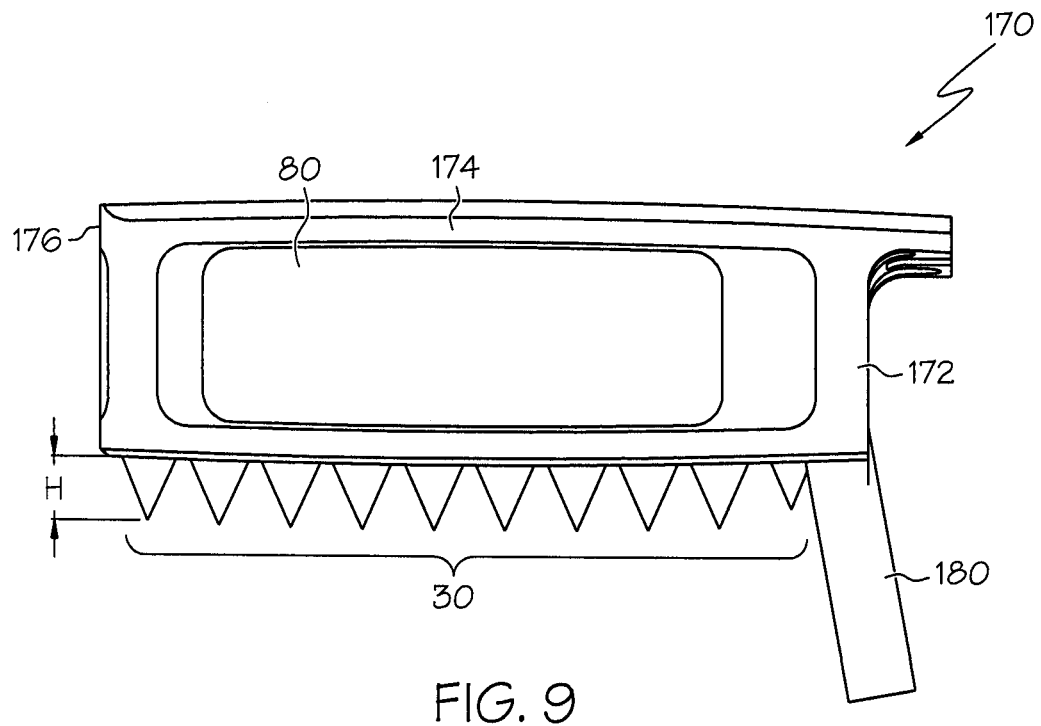
FIG. 9 is an anterior view of the implant device of FIG. 8.
Figure 10:
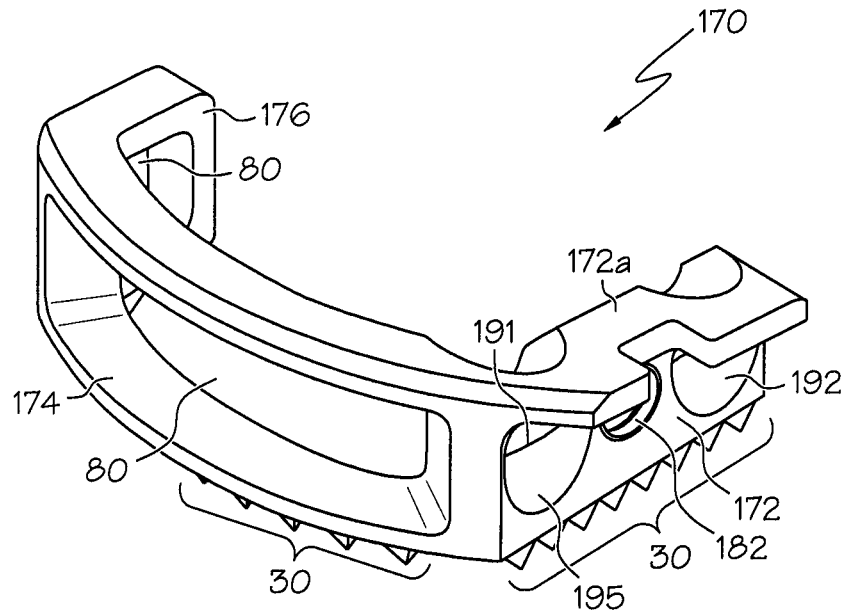
FIG. 10 is an angled lateral side perspective view of an implant device in accordance with an aspect of the present invention.
Figure 11:
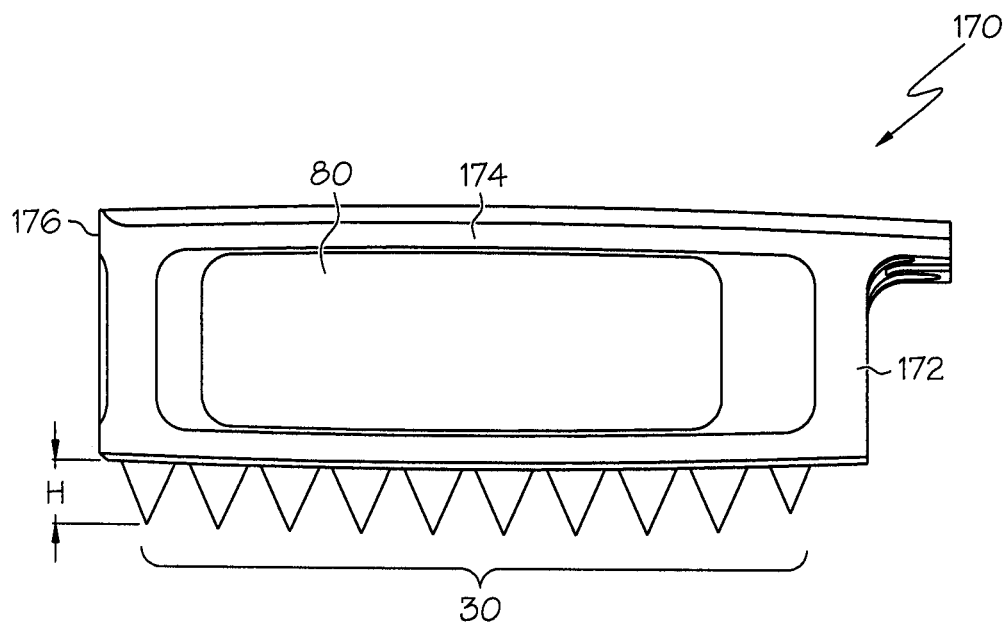
FIG. 11 is an anterior view of the implant device of FIG. 10.

As further shown in FIGS. 8 and 9, a bottom mounting member 180 can extend downward from and at an angled relative to the lateral mounting portion 172. The lateral mounting portion 172 and bottom mounting member 180 are arranged relative to each other so that their front surfaces form an angle greater than 90° and less than 180°, preferably from 110° to about 175°, and more preferably from 150° to 170°. The angle at which the lateral mounting portion 172 and bottom mounting member 180 are joined is provided so that bone fasteners 50 can be introduced through the base member 170 at desired angles. Accordingly, the base member 170 can be designed in any other manner that permits the bone fasteners to be introduced therethrough at the desired angles. In an alternative embodiment, as shown in FIGS. 10 and 11, the lateral mounting portion 172 can be configured without a bottom mounting member 180 extending downward.

The bottom mounting member 180 includes at least one aperture configured for receiving a bone fastener. The bottom mounting member 180 of FIG. 8 includes an aperture 194 in the form of an elongated slot having an elongation length. The bone fastener is introduced into the slot 194 and into a vertebra. The slot 194 is configured such that a bone fastener can slide and rotate along the elongation length of the slot 194 relative to the base member 170. Thus, in use, as two adjacent vertebrae, to which the base member 170 is fixed, collapse or settle and move toward each other, the bone fastener contained within the slot 194 will slide and move with the vertebra into which it extends in a direction toward base member 170 and the other vertebra.

Figure 13:
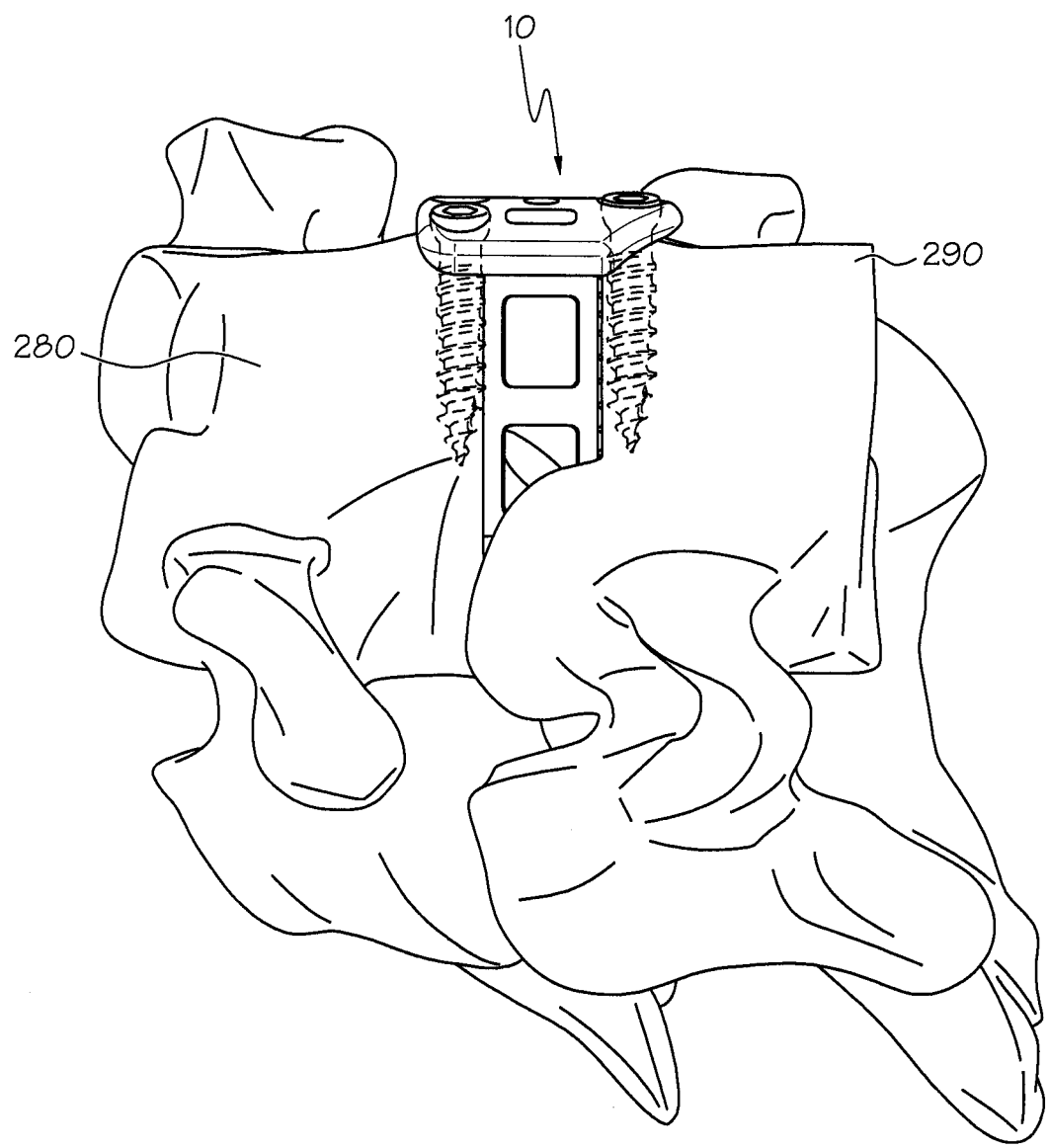
FIG. 13 is an angled anterior perspective view of an implant device positioned between two vertebrae in accordance with an aspect of the present invention.
Figure 14:
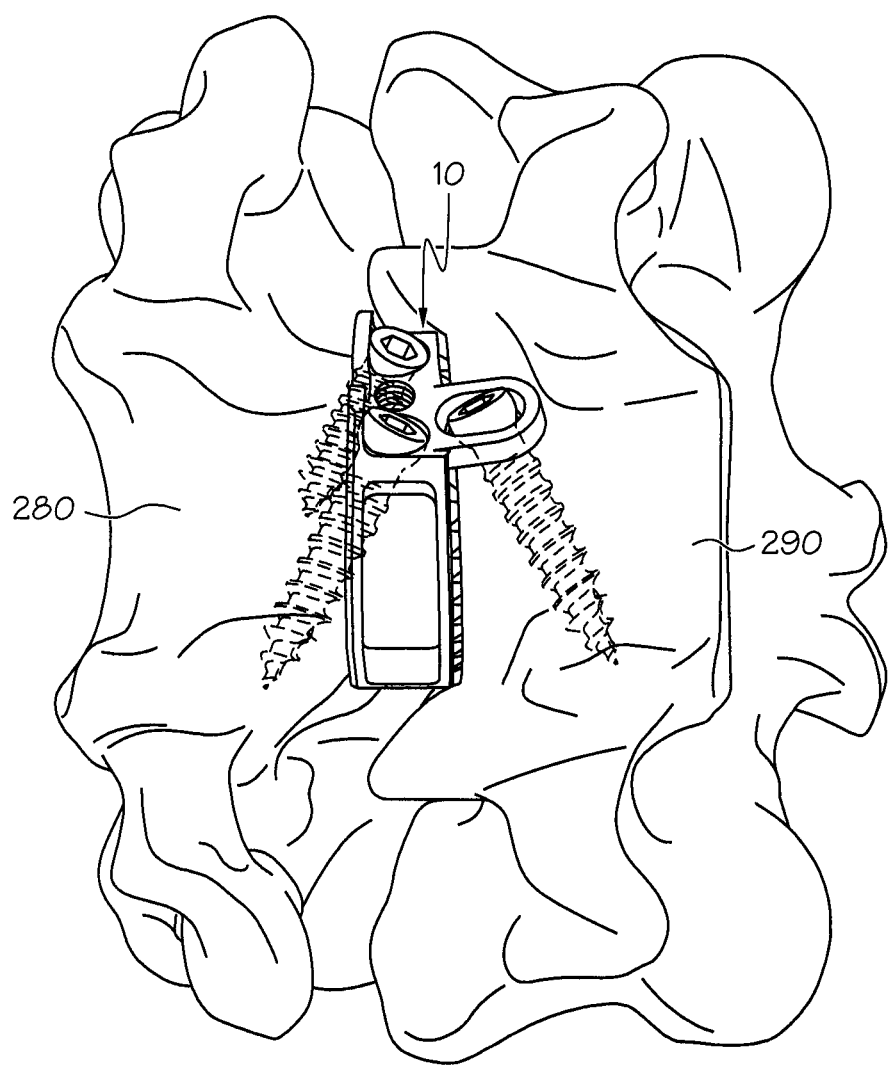
FIG. 14 is an angled lateral side perspective view of an implant device positioned between two vertebrae in accordance with an aspect of the present invention.

FIGS. 12 through 14 illustrate example embodiments of the implant device 10 secured between two spinal vertebrae 280, 290. FIG. 12 illustrates the lateral mounting portion of the device 10 positioned on the left-hand, lateral side of a spinal column. This view shows the elongated side portion of the implant device 10 extending along the anterior peripheral side of the spinal column vertebrae 280, 290. The apertures of the lateral mounting portion are aligned with respect to the adjacent vertebrae 280, 290 positioned above and below the device. From this position, bone fasteners 50 can be inserted through the apertures, at an angle if desired, and into the adjacent vertebrae in order to secure the device 10. The bone fasteners 50 are inserted into the vertebrae 280, 290 sufficiently so that the convex spherical head of the fasteners rests against the seats of the apertures. In a similar fashion, FIGS. 13 and 14 illustrate the device positioned between vertebral bodies 280 and 290. The elongated side portion of the device 10 corresponds to the anterior peripheral side of the vertebral bodies 280, 290. As shown, bone fasteners extend through the apertures in the lateral mounting portion into the vertebral bodies 280 and 290. Although not shown, an enhanced fit of the lateral mounting portion can be achieved by trimming or otherwise removing a few millimeters of bone from a lip osteophyte of the vertebral bodies to provide a substantially flat or angled surface, which ever best aligns with the shape of the lateral mounting portion. The trimmed surface provides a substantially flush surface for anchoring bone fasteners into the vertebral bodies. The substantially flush surface can also accommodate the sliding of the lateral mounting portion as the interface members subside into the vertebral bodies.

Many surgical techniques for inserting the implant device 10 are contemplated. Specific feasibility, benefits and surgical advantages are not discussed in detail herein. In theory, however, it is thought that a lateral insertion technique may generally provide shorter hospital stays and be less painful than traditional insertion approaches to the spine such as anterior or posterior insertion. For instance, a lateral insertion method may be minimally invasive to the anterior region of the spine housing soft and delicate organs and avoids an incision that traverses the abdomen and cutting or disrupting the muscles of the back. In any case, the examples presented below are also not to be construed as being preferred, beneficial or the like.

Figure 15:
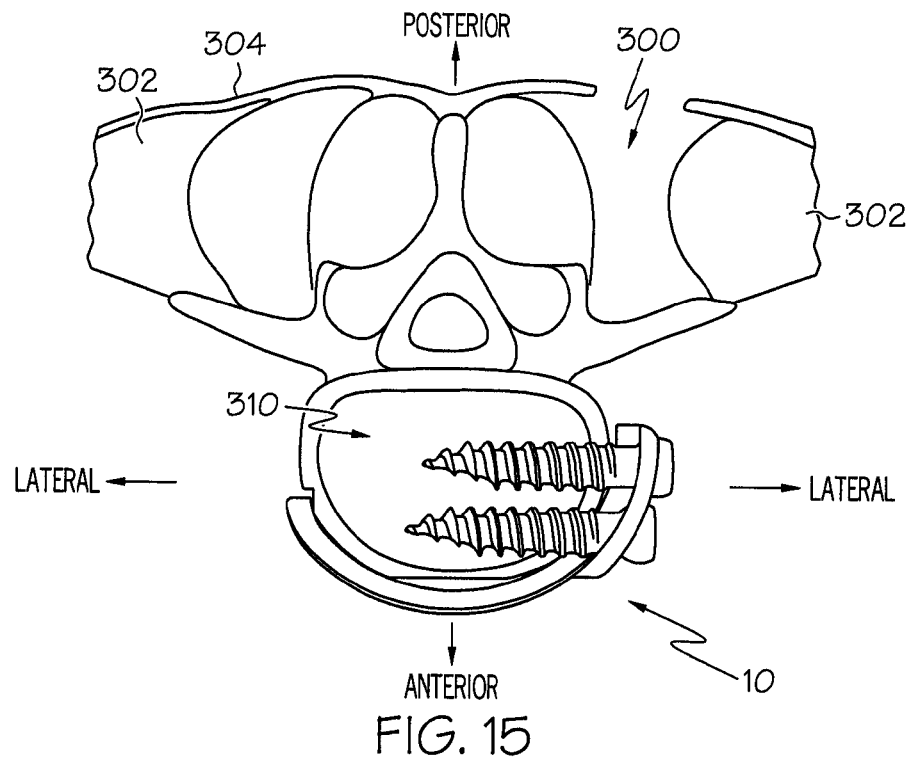
FIG. 15 is a top view of a posterior lateral opening along a spine that is suitable for inserting an implant device to be secured to a lateral side of a vertebra.
Figure 16:
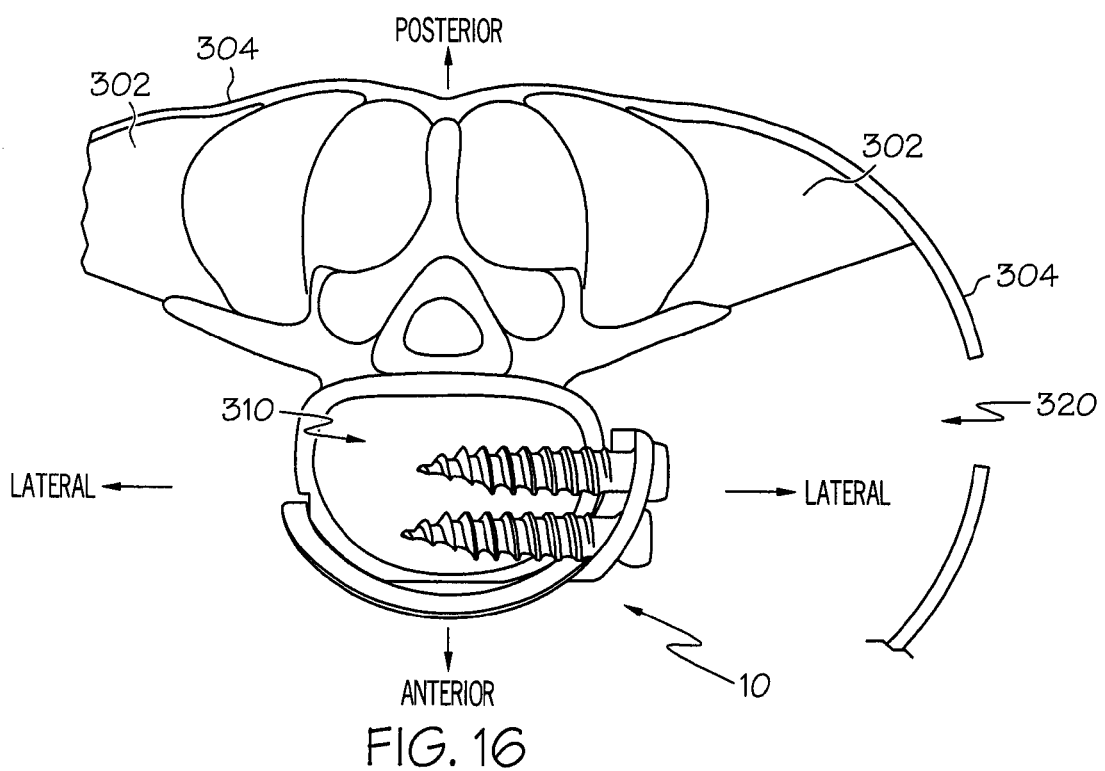
FIG. 16 is a top view of a lateral opening that is suitable for inserting an implant device to be secured to a lateral side of a vertebra.

The implant device 10 and corresponding embodiments thereof can be suitable for use in a posterior lateral (i.e. postero-lateral) or lateral insertion method, as generally illustrated in FIGS. 15 and 16, which shows a postero-lateral and lateral insertion opening 300, 320 exposing a lateral side of a vertebra 310, respectively. The implant device 10 can be inserted through the postero-lateral opening 300 or the lateral opening 320 in order to position the device 10 between two adjacent vertebrae. The postero-lateral opening 300 and lateral opening 320 are formed by creating an incision in the outer flesh or skin 304 of a patient. In a postero-lateral insertion technique, the posterior musculate 302 of the spine can be separated to provide a shorter approach to a lateral side of the vertebrae. An insertion tool as known in the art can be used to position the implant device 10 and rotate the device around fusion material if desired. Once the implant device 10 is in position, the bone fasteners can be inserted through corresponding apertures in the lateral mounting portion into the vertebrae. In a lateral insertion technique, the vertebra 310 is accessed from an opening 320 on the patient's left or right lateral side. From the opening 320, disk material may be removed and replaced with fusion material along with the implant device 10. It is further contemplated that the configuration of the implant device 10 described herein can be modified in order to accommodate insertion from either lateral side of the patient's spine.

While shown embodiments of the present invention are described for supporting adjacent lumbar vertebrae, persons skilled in the art would recognize that the bone pate of the present invention may be utilized in other regions of the spine. Further, the device and method of the invention is not limited to vertebral bodies, but can also be use to join two other pieces of bone in other parts of the body.

While embodiments and applications of the present invention have been shown and described, it would be apparent to those skilled in the art that many more modifications are possible without departing from the inventive concepts herein. The invention, therefore, is not to be restricted except in the spirit of the appended claims.

What is claimed is:

1. An implant device for the spine, the implant device including:
   a base member configured to interface with two adjacent vertebrae including a lateral mounting portion, located on only one side of an anterior-posterior dividing line, to accommodate fixation of the device to a lateral side of at least one of the vertebrae, with the lateral side of at least one of the vertebrae being located on the same one side of the anterior-posterior dividing line, and an elongated side portion extending from a side of the lateral mounting portion and configured to extend between the vertebrae;
   at least one interface member extending from at least one surface of the elongated side portion, the at least one interface member being configured to provide controlled subsidence of the implant device into the at least one vertebra subsequent to implantation; and
   a plurality of bone fasteners extending through apertures provided in the lateral mounting portion of the base member to penetrate the lateral side of the at least one of the vertebrae.

2. The implant device of claim 1, wherein the device is positioned between the two vertebrae through a posterior lateral opening exposing a lateral side of the vertebrae.

3. The implant device of claim 1, wherein the device is positioned between the two vertebrae through a lateral opening exposing a lateral side of the vertebrae.

4. The implant device of claim 1, wherein the at least one interface member includes a plurality of interface members extending from the at least one surface of the elongated side portion, wherein at least one of the plurality of interface members is aligned with an elongate direction of the spine.

5. The implant device of claim 4, wherein the elongated side portion has a bottom surface, the plurality of interface members extend from the bottom surface of the elongated side portion.

6. The implant device of claim 4, wherein at least some of the plurality of interface members extend from at least one of top and bottom surfaces of the elongated side portion.

7. The implant device of claim 4, wherein the plurality of interface members extend from more than one surface of the elongated side portion.

8. The implant device of claim 1, wherein no relative sliding movement occurs between the plurality of fasteners and the base member during the controlled subsidence.

9. The implant device of claim 1, wherein at least one of the apertures is an elongated slot having an elongation length, wherein the slot is configured to permit relative travel movement of the respective bone fastener extending therethrough along the elongation length of the slot during the controlled subsidence.

10. The implant device of claim 9, wherein the lateral mounting portion further includes at least one aperture in the form of a round hole, the round hole being configured for receiving a bone fastener extending therethrough.

11. The implant device of claim 9, wherein the elongation length is greater than a height of the at least one interface member.

12. The implant device of claim 9, wherein the elongation length is less than a height of the at least one interface member.

13. The implant device of claim 9, wherein relative travel movement occurs between at least one fastener and the base member during the controlled subsidence.

14. The implant device of claim 9, wherein the at least one interface member is substantially fully penetrated into the at least one vertebra during controlled subsidence and the bone fastener is not at the end of the elongated slot.

15. The implant device of claim 9, wherein the bone fastener is at an end of the elongated slot before the at least one interface member is substantially fully penetrated into a vertebra during controlled subsidence.

16. The implant device of claim 1, further including a restraining means for restricting movement of at least one bone fastener extending through an aperture in the lateral mounting portion.

17. The implant device of claim 16, wherein the restraining means includes a cover extending over a portion of at least one bone fastener for preventing back-out of the bone fastener.

18. The implant device of claim 16, wherein the restraining means includes a restraining plate secured to the lateral mounting portion via a fastener to mitigate the backing out of a bone fastener, the restraining plate being configured to permit at least one bone fastener to slide and toggle in the aperture the at least one bone fastener extends through.

19. The implant device of claim 1, wherein the elongated side portion is curved and has a posterior face and an anterior face relative to the vertebrae.

20. The implant device of claim 19, wherein the posterior face of the elongated side portion is concave and the anterior face of the elongated side portion is convex.

21. The implant device of claim 19, wherein the lateral mounting portion is contiguous with one end of the elongated side portion.

22. The implant device of claim 19, wherein the base member further includes a back portion being contiguous with the elongated side portion.

23. The implant device of claim 1, wherein the elongated side portion forms a peripherally-surrounded chamber for receiving fusion material, wherein the lateral mounting portion forms a segment of the peripherally-surrounded chamber.

24. The implant device of claim 23, wherein the peripherally-surrounded chamber includes at least one interior compartment.

25. The implant device of claim 23, wherein the peripherally-surrounded chamber includes at least one interior member extending from an inner face surface of the elongated side portion, and the at least one interior member being configured to divide the peripherally-surrounded chamber into at least two interior compartments.

26. The implant device of claim 25, wherein the peripherally-surrounded chamber has a top surface and a bottom surface.

27. The implant device of claim 23, wherein the peripherally-surrounded chamber includes a substantially flat inner face surface having an interior member extending from a portion of the inner surface and the interior member being connected to the opposing portion of the inner face surface of the peripherally-surrounded chamber such that the chamber is divided into two interior compartments.

28. The implant device of claim 23, wherein the at least one interface member includes a plurality of interface members extending from at least one surface of the peripherally-surrounded chamber, wherein at least one of the plurality of interface members is aligned with an elongate direction of the spine.

29. The implant device of claim 1, further including a bottom mounting member extending from a surface of the lateral mounting portion at an angle relative to the lateral mounting portion.

30. The implant device of claim 29, wherein the bottom mounting member includes at least one aperture configured to receive a bone fastener therethrough.

31. The implant device of claim 30, wherein at least one aperture in the lateral mounting portion is in the form of an angled round hole relative to another aperture.

32. The implant device of claim 31, wherein the at least one aperture in the bottom mounting member is an elongated slot.

33. An implant device for a spine, the implant device including:
  a base member including a lateral mounting portion, located on only one side of a dividing line extending along an anterior-posterior direction, to accommodate fixation of the device to a lateral side of at least one vertebra, with the lateral side of at least one of the vertebrae being located on the same one side of the anterior-posterior extending dividing line, and an elongated side portion extending from a side of the lateral mounting portion in a direction towards the at least one vertebra, wherein the elongated side portion interfaces with the at the at least one vertebra;
  at least one interface member extending from at least one surface of the elongated side portion, the at least one interface member being configured to provide controlled subsidence of the implant device into the at least one vertebra;
  a plurality of bone fasteners extending through apertures provided in the lateral mounting portion of the base member; and
  a restraining means for restricting movement of at least one bone fastener.

34. The implant device of claim 33, wherein the elongated side portion extends between two vertebrae.

35. The implant device of claim 34, wherein the at least one interface member includes a plurality of interface members extending from the at least one surface of the elongated side portion, wherein at least one of the plurality of interface members is aligned with an elongate direction of the spine.

36. The implant device of claim 34, wherein the elongated side portion has a top surface and a bottom surface.

37. The implant device of claim 36, wherein the lateral mounting portion has a segment extending above the top surface of the elongated side portion and a segment extending below the bottom surface of the elongated side portion.

38. The implant device of claim 37, wherein the segment extending above the top surface of the elongated side portion includes at least one aperture and the segment extending below the bottom surface of the elongated side portion includes at least one aperture.

39. The implant device of claim 38, wherein no relative sliding movement occurs between the plurality of fasteners and the base member during the controlled subsidence.

40. The implant device of claim 38, wherein the at least one aperture of the segment extending above the top surface of the elongated side portion is in the form of a round hole.

41. The implant device of claim 38, wherein the at least one aperture of the segment extending below the bottom surface of the elongated side portion is in the form of an elongated slot.

42. The implant device of claim 41, wherein the elongated slot has an elongation length and the elongated slot is configured to permit relative travel of the respective bone fastener extending therethrough along the elongation length of the slot during the controlled subsidence.

43. The implant device of claim 34, wherein the elongated side portion forms a peripherally-surrounded chamber for receiving fusion material, wherein the lateral mounting portion forms a segment of the peripherally-surrounded chamber.

44. The implant device of claim 43, wherein the peripherally-surrounded chamber includes at least two interior compartments.

45. The implant device of claim 43, wherein the peripherally-surrounded chamber includes at least one interior member extending from an inner face surface of the elongated side portion, and the at least one interior member being configured to divide the peripherally-surrounded chamber into at least two interior compartments.

46. The implant device of claim 33, wherein the device is positioned between two vertebrae through a posterior lateral opening exposing the lateral side of the vertebrae.

47. The implant device of claim 33, wherein the device is positioned between two vertebrae through a lateral opening exposing the lateral side of the vertebrae.

* * * * *

UNITED STATES PATENT AND TRADEMARK OFFICE
CERTIFICATE OF CORRECTION

PATENT NO. : 8,613,772 B2
APPLICATION NO. : 11/686054
DATED : December 24, 2013
INVENTOR(S) : Robert S. Bray et al.

It is certified that error appears in the above-identified patent and that said Letters Patent is hereby corrected as shown below:

In the Claims:

Column 14, line 2, claim 1 please delete "the spine" and insert --a spine--.

Signed and Sealed this
Fifteenth Day of April, 2014

Michelle K. Lee
*Deputy Director of the United States Patent and Trademark Office*